United States Patent [19]

Englert et al.

[11] Patent Number: 4,921,875

[45] Date of Patent: May 1, 1990

[54] USE OF AMINO-SUBSTITUTED BENZOIC ACIDS AS REMEDIES FOR DIARRHEA, AND MEDICAMENTS BASED ON THESE COMPOUNDS

[75] Inventors: Heinrich C. Englert, Hofheim am Taunus; Max Hropot, Flörsheim am Main; Hans-Jochen Lang, Hofheim am Taunus; Rainer Greger, Heitersheim, all of Fed. Rep. of Germany

[73] Assignees: Hoechst Aktiengesellschaft, Frankfurt am Main; Max-Planck-Gesellschaft Zur Forderung Der Wissenschaften, Gottingen, both of Fed. Rep. of Germany

[21] Appl. No.: 25,580

[22] Filed: Mar. 13, 1987

[30] Foreign Application Priority Data

Mar. 15, 1986 [DE]  Fed. Rep. of Germany ....... 3608726

[51] Int. Cl.$^5$ .................... A61K 31/195; A61K 31/44; A61K 31/40
[52] U.S. Cl. ..................................... 514/567; 514/277; 514/337; 514/427; 514/564; 514/867
[58] Field of Search ............... 514/277, 337, 427, 564, 514/567, 867

[56] References Cited

U.S. PATENT DOCUMENTS 4,024,279  5/1977  Zor et al. ............................ 514/867
4,029,815  6/1977  Sherlock et al. .................... 514/867

Primary Examiner—Frederick E. Waddell
Attorney, Agent, or Firm—Finnegan, Henderson, Farabow, Garrett and Dunner

[57] ABSTRACT

A description is given of the use of amino-substituted benzoic acid derivatives of the formula I

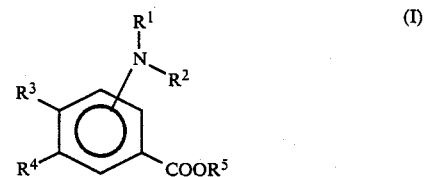

in which $R^1$ and $R^2$ denote hydrogen, (cyclo)alkyl, unsubstituted or substituted phenyl or naphthyl, or $R^1$ and $R^2$ together denote a chain —$(CH_2)_m$— with m=3 to 6, or together denote a chain —$(CH=CH)_n$— with n equal to 2 or 3; $R^3$ denotes hydrogen, halogen or alkyl; $R^4$ denotes hydrogen or $NO_2$; $R^5$ denotes hydrogen or a radical which can be eliminated under physiological conditions; for the preparation of a remedy for diarrhea.

2 Claims, No Drawings

USE OF AMINO-SUBSTITUTED BENZOIC ACIDS AS REMEDIES FOR DIARRHEA, AND MEDICAMENTS BASED ON THESE COMPOUNDS

The invention relates to the use of amino-substituted benzoic acid derivatives of the formula I

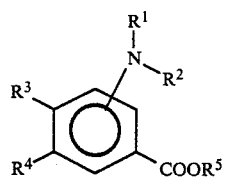

in which
$R^1$ and $R^2$, which can be identical or different, denote hydrogen,
($C_1$–$C_6$)-alkyl, straight-chain or branched,
($C_4$–$C_8$)-cycloalkyl,
Ar which, in each case, denotes phenyl or naphthyl which is unsubstituted or substituted 1–3 times, identically or differently, by ($C_1$–$C_2$)-alkyl, ($C_1$–$C_2$)-alkoxy, F, Cl, Br, I, OH, $NH_2$, $C_6H_5$—NH or $CF_3$,
together denote a chain —$(CH_2)_m$— with $m=3$ to 6, which is unsubstituted or substituted by 1–2 methyl groups, or
together denote a chain —$(CH=CH)_n$—, with n equal to 2 or 3, which is unsubstituted or substituted with 1 or 2 methyl groups,
$R^3$ denotes hydrogen, F, Cl, Br, I or ($C_1$–$C_6$)-alkyl,
$R^4$ denotes hydrogen or $NO_2$,
$R^5$ denotes hydrogen or a radical which can be eliminated under physiological conditions,
and in which the substituent $NR^1R^2$ is in the meta or ortho position with respect to the carboxyl group, for the preparation of a remedy for diarrhea.

In many cases, compounds of the formula I are already known. Thus, for example, compounds I with $R^3$, $R^4$, $R^5$ and $R^1$=H, and $R^2$=Ar with Ar having the abovementioned meaning, have been described as antirheumatic and antiinflammatory agents (Arzneimittelforschung/Drug Res. 33 (1), No. 4 a, 1983, 621–627). Taking the example of meclofenamic acid

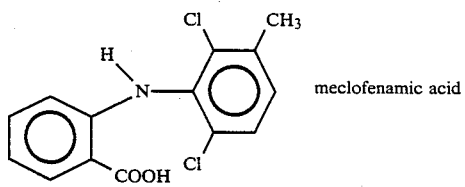

it has been shown that it induces diarrhea as a side effect (Ibid.: 631–635). Thus, it was extremely surprising that compounds of the formula I, in particular those which have no or only weak antirheumatic properties, are, very much in contrast, very suitable for the treatment of diarrhea, in particular for the treatment of those types of diarrhea induced by bacterial toxins such as, for example, the cholera toxin.

Thus the invention relates to medicaments which contain compounds of the general formula I, and to their use for the treatment of diarrhea.

It is preferred to use those compounds of the formula I in which $R^1$ represents cyclic alkyl having 5 to 7 ring members or represents Ar in the abovementioned meaning, $R^2$ represents H, $R^3$ represents H, alkyl having 1–2 carbon atoms, chlorine or bromine, $R^4$ represents H or $NO_2$, $R^5$ represents H, and the radical

is located in the ortho position with respect to the carboxyl group.

When compounds having $R^1/R^2$ in the meaning of Ar are used, the total number of carbon atoms in $R^1$ and $R^2$ is preferably up to 15, in particular up to 9.

It is likewise preferred to use for controlling diarrhea compounds I in which
$R^1$ and $R^2$ form
(a) a saturated —$(CH_2)_m$— chain with $m=4$–6 or
(b) a doubly unsaturated —$(CH=CH)_n$— chain with $n=2$,
$R^3$ represents alkyl having 1–2 carbon atoms or chlorine or bromine,
$R^4$ represents hydrogen, and $R^5$ represents hydrogen, and the radical

is located in the meta position with respect to the carboxyl group.

The following compounds are especially well suited for the treatment of diarrhea:
(1) 4'-ethoxydiphenylamine-2-carboxylic acid[3]
(2) 2-(1-naphthylamino)benzoic acid[3]
(3) 2'-aminodiphenylamine-2-carboxylic acid[3]
(4) 4'-anilino-5-nitrodiphenylamine-2-carboxylic acid[3]
(5) 4'-trifluoromethyl-4-nitrodiphenylamine-2-carboxylic acid
(6) 2-cyclooctylamino-5-nitrobenzoic acid[4]
(7) 2-cyclohexylamino-5-nitrobenzoic acid[4]
(8) diphenylamine-2-carboxylic acid[1]
(9) 4'-methyldiphenylamine-2-carboxylic acid[3]
(10) 4'-chlorodiphenylamine-2-carboxylic acid[3]
(11) 4'-nitrodiphenylamine-2-carboxylic acid
(12) 4'-bromodiphenylamine-2-carboxylic acid[4]
(13) 3',4'-dichlorodiphenylamine-2-carboxylic acid[1]
(14) 2'-hydroxydiphenylamine-2-carboxylic acid[3]
(15) 2'-methoxydiphenylamine-2-carboxylic acid[3]
(16) 5-chlorodiphenylamine-2-carboxylic acid
(17) 3',5-dichlorodiphenylamine-2-carboxylic acid
(18) 3'-trifluoromethyl-5-chlorodiphenylamine-2-carboxylic acid
(19) 4-methyl-3-N-pyrrolidinobenzoic acid
(20) 4-chloro-3-N-pyrrolidinobenzoic acid
(21) 4-chloro-3-N-pyrrolobenzoic acid
(22) 4-chloro-3-anilinobenzoic acid.

Citations (1) Arzneimittelforschung/Drug Res. 33 (1), No. 4a, 1983 621–627
(2) Ibid.: 631–635
(3) Liebigs Ann. Chem. 355, 312–348
(4) Berichte 39, 1694

PREPARATION OF THE COMPOUNDS I

Where not already known from the literature, the compounds I were prepared by the following processes:

(a) From the 2-chloro- or 2-bromobenzoic acid of the formula II and an amine ArNH$_2$, Ar having the abovementioned meaning, under the action of Cu powder, by methods known per se[3)]

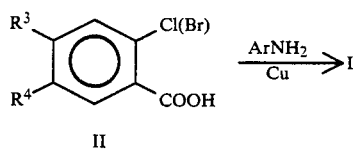

The following compounds were prepared in this way:
No. 4, melting point: 232° C.
No. 16, melting point: 204°–206° C.
No. 17, melting point: 200°–203° C.
No. 18, melting point: 212°–214° C.

(b) By an exchange reaction of chloro(bromo)benzoic acids II, with R$^4$ having the meaning of NO$_2$, and an amine

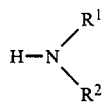

with R$^1$ and R$^2$ having the abovementioned meaning, without Cu catalysis, in a dipolar aprotic solvent such as dimethylacetamide, at temperatures of 100°–180° C.

The following compounds were prepared:
No. 4, melting point: 232° C.
No. 5, melting point: 303°–306° C. as Na salt
No. 6, melting point: 194°–196° C.
No. 7, melting point: 186°–189° C.

(c) From the methyl 3-aminobenzoates III with cyclic acid anhydrides IV are obtained amides of the formula V

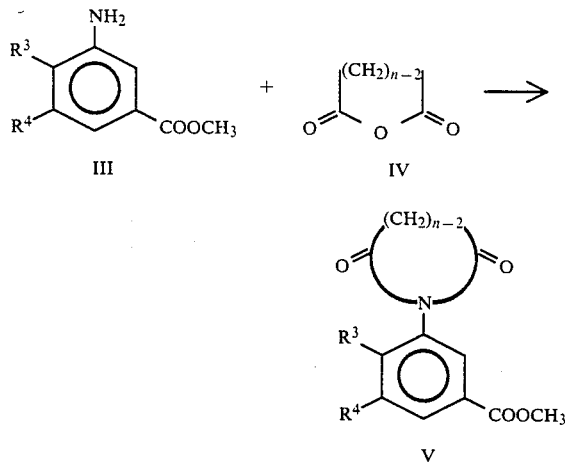

with m having the abovementioned meaning. V can be reduced with NaBH$_4$/BF$_3$.Et$_2$O in diglyme to give VI:

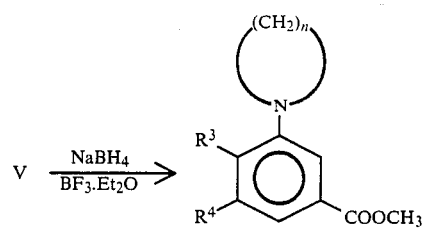

The esters VI are hydrolyzed by standard methods to give compounds I. The reaction sequence is described in the literature (W. Merkel, D. Mania, D. Bormann, Liebigs Ann. Chem. 1979, 461–469). The following compounds were prepared in this way:
No. 19, melting point: 163°–165° C.
No. 20, melting point: 155°–157° C.

(d) From methyl 3-bromobenzoates VII and acetanilides VIII with Cu catalysis (Ullmann-Goldberg reaction) by methods known per se (A. S. Freeman, J. R. Butter, L. D. Freedmann, J. Org. Chem. 1978, 43 4975–4978).

Ar having the abovementioned meaning, and Ac representing the acetyl group. The compounds IX are hydrolyzed by standard methods to give the compounds I.

Compounds prepared:
No. 22, melting point: 223° C.

(e) From the 3-aminobenzoic esters III and 2,5-dimethoxytetrahydrofurans are obtained compounds X in a manner known per se (N. Elening, Clauson-kaas, Acta Chem. Scand. 6, 876 (1952)).

Compounds X are hydrolyzed in a manner known per se to give compounds I.

Compound prepared:
No. 21, melting point: 222°–223° C.

The compounds of the formula I which are used according to the invention, and their pharmaceutically tolerated salts—particularly suitable in this context are the alkali metal and alkaline earth metal salts, such as Na+, K+, NH4+ or Ca++ salts, but salts of organic bases such as ethanolamine salt are also of importance—are agents for the treatment of diarrhea. They are administered enterally, for example orally, in daily doses of at least 0.01 mg/kg, preferably 0.05 mg/kg, in particular 10 mg/kg, to a maximum of 200 mg/kg, preferably 50 mg/kg body weight and, in particular, 20 mg/kg, based on an adult weighing 75 kg, in capsules, coated tablets, tablets or solutions, alone or in combination with electrolyte solutions which counteract the dehydration associated with diarrhea. They are suitable for the treatment of all diseases in which there is a pathological increase in the loss of water and chloride by the intestines, such as occurs in the very wide variety of types of diarrhea, especially in toxic diarrhea resulting from infectious diseases such as, for example, cholera, or in hereditary types of diarrhea, such as congenital chloride diarrhea.

The daily doses are administered in 1 to 8, preferably 3–6, single doses.

The compounds I are used either in the pure form or together with generally known pharmaceutically acceptable auxiliaries.

$R^5$ is preferably hydrogen, but can also be every suitable group which is eliminated under physiological conditions and thus provides the free COOH group or its salts.

We claim:

1. A method of treating diarrhea in a patient which comprises the step of administering thereto an effective amount of a compound selected from the group consisting of
   4'-ethoxydiphenylamine-2-carboxylic acid,
   2-(1-naphthylamino)benzoic acid,
   2'-aminodiphenylamine-2-carboxylic acid,
   4'-anilino-5-nitrodiphenylamine-2-carboxylic acid,
   4'-trifluoromethyl-4-nitrodiphenylamine-2-carboxylic acid,
   2-cyclooctylamino-5-nitrobenzoic acid,
   2-cyclohexylamino-5-nitrobenzoic acid, diphenylamine-2-carboxylic acid,
   4'-methyldiphenylamine-2-carboxylic acid,
   4'-chlorodiphenylamine-2-carboxylic acid,
   4'-nitrodiphenylamine-2-carboxylic acid,
   4'-bromodiphenylamine-2-carboxylic acid,
   3',4'-dichlorodiphenylamine-2-carboxylic acid,
   2'-hydroxydiphenylamine-2-carboxylic acid,
   2'-methoxydiphenylamine-2-carboxylic acid,
   5-chlorodiphenylamine-2-carboxylic acid,
   3',5-dichlorodiphenylamine-2-carboxylic acid,
   3'-trifluoromethyl-5-chlorodiphenylamine-2-carboxylic acid,
   4-methyl-3-N-pyrrolidinobenzoic acid,
   4-chloro-3-N-pyrrolidinobenzoic acid,
   4-chloro-3-N-pyrrolobenzoic acid and
   4-chloro-3-anilinobenzoic acid
together with a pharmaceutically acceptable carrier.

2. A method of treating diarrhea in a patient which comprises the step of administering thereto an effective amount of the compound 3',5-dichlorodiphenylamine-2-carboxylic acid.

* * * * *